United States Patent [19]

Abe et al.

[11] Patent Number: 4,863,952

[45] Date of Patent: Sep. 5, 1989

[54] METHOD OF PROMOTING PERCUTANEOUS DRUG ABSORPTION WITH 2-PYRROLIDIN-2-ONE 5-CARBOXYLIC ACIDS AND ESTERS THEREOF

[75] Inventors: Yoko Abe; Susumu Satoh; Yoshiaki Itoh, all of Ibaraki, Japan

[73] Assignee: Nitto Electric Industrial Co., Ltd., Osaka, Japan

[21] Appl. No.: 784,303

[22] Filed: Oct. 4, 1985

[30] Foreign Application Priority Data

Oct. 26, 1984 [JP] Japan ................... 59-226279

[51] Int. Cl.$^4$ .................. A61K 9/00; A61K 31/40
[52] U.S. Cl. ..................... 514/423; 548/534
[58] Field of Search ............. 548/551, 534; 514/423

[56] References Cited

U.S. PATENT DOCUMENTS

| | | | |
|---|---|---|---|
| 3,836,665 | 9/1974 | Eberhardt et al. | 514/423 |
| 3,920,814 | 11/1975 | Bocher et al. | 548/534 |
| 3,975,399 | 8/1976 | DeFranco et al. | 548/551 |
| 4,394,380 | 7/1983 | Hassain et al. | 514/652 |
| 4,428,883 | 11/1984 | Hassain | 514/562 |

FOREIGN PATENT DOCUMENTS 0123948 11/1984 European Pat. Off. ............ 548/534
2102173 8/1972 Netherlands ...................... 548/534

OTHER PUBLICATIONS

Zoretic et al., J. Hetero. Chem., 14 pp. 1267–1269 (1977).

Primary Examiner—David B. Springer
Attorney, Agent, or Firm—Wenderoth, Lind & Ponack

[57] ABSTRACT

A composition for percutaneous drug administration which contains a compound of the general formula

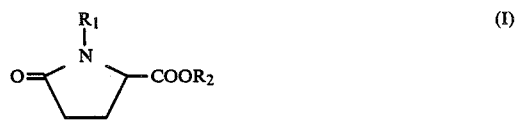

(I)

wherein $R_1$ is a hydrogen atom or an alkyl group and $R_2$ is a residue of aliphatic hydrocarbon.

The composition is capable of promoting percutaneous drug absorption.

19 Claims, 2 Drawing Sheets

METHOD OF PROMOTING PERCUTANEOUS DRUG ABSORPTION WITH 2-PYRROLIDIN-2-ONE 5-CARBOXYLIC ACIDS AND ESTERS THEREOF

BACKGROUND OF THE INVENTION

1. Field of the Invention

This invention relates to a composition for percutaneous drug adminstration which is capable of promoting percutaneous drug absorption and a method of promoting percutaneous drug absorption.

2. Description of the Prior Art

Hithertofore the purpose of the application of a drug composition to the skin has been to produce some or other local effect on the skin or subcutaneous tissues, disinfectant, analgesic, itch-killing or antiinflammatory effect. For the purpose of producing a systemic effect, oral administration of tablets or injection has been made use of so far. Tablets for oral administration are, however, have drawbacks: active ingredients are liable to primary metabolism in the liver after their absorption, or they are absorbed only to an insufficient extent, or, when a lasting effect is desired, an unnecessarily high concentration in the body is reached, although temporarily. Oral administration of indomethacin, for instance, produces on gastrointestinal disorders. Administration by injection, on the other hand, can result in rapid absorption but requires skilled persons such as physicians.

In recent years it has been proposed to administer drugs percutaneously for the purpose of producing a systemic effect to thereby alleviate or overcome the above-mentioned adverse effects or drawbacks.

Percutaneous administration of drugs is advantageous, for example, in that the effects of the drugs can be easily maintained, that the drug concentration in the body can be controlled, or that the drugs scarcely undergo primary metabolism in the liver because they enter the blood circulation through cutaneous tissues.

However, the skin, when normal, essentially has the so-called barrier function to prevent invasion of foreign substances into the body. Therefore the administration of drugs via the skin has been limited to local uses. For the purpose of producing a systemic effect, an auxiliary agent for promoting percutaneous absorption is required and recent proposals include various substances. Thus, for example, U.S. Pat. No. 3,551,554 discloses dimethyl sulfoxide, and also dimethylacetamide, dimethylformamide, methyl decyl sulfoxide, and so forth.

Also known are absorption-promoting agents in combination with lower alkylamide, for exmaple, combinations of dimethylacetamide and ethyl alcohol, isopropyl alcohol or isopropyl palmitate (U.S. Pat. No. 3,472,931) or combinations of 2-pyrrolidone and an appropriate oil or an ester between an straight-chain fatty acid and an alcohol (U.S. Pat. No. 4,017,641). However, they are not yet fully satisfactory as absorption-promoting agents with respect to their effect, safety and feel upon use.

SUMMARY OF THE INVENTION

An object of the invention is to provide compositions for percutaneous drug administration which are capable of promoting percutaneous drug absorption.

Another object of the invention is to provide a method of promoting percutaneous drug absorption.

The present inventors made intensive investigations to solve such problems and, as a result, found that compounds of the general formula:

wherein $R_1$ is a hydrogen atom or an alkyl group and $R_2$ is a residue of aliphatic hydrocarbon (hereinafter these compounds are referred to as "PCA esters"), can promote skin permeation and percutaneous absorption of drugs and that said hydrocarbyl ester compounds can be used each as one of base components in producing preparations containing drugs applicabe to the skin.

The present invention, that has been completed on the above findings, consists in the following:

(1) A composition for percutaneous drug administration which contains at least one ester compound selected from among the PCA esters;

(2) A composition for percutaneous drug administration which further contains a drug substance; and (3) A method of promoting percutaneous drug absorption which comprises administering a drug percutaneously in the presence of at least one ester compound selected from among the PCA esters.

BRIEF DESCRIPTION OF THE DRAWINGS

In the accompanying drawings, FIG. 1 and FIG. 2 each illustrates the effect of the present invention graphically.

DETAILED DESCRIPTION OF THE INVENTION

The PCA esters are so far known as emollients and are used in cosmetics or toiletries. It is also known that pyrrolidonecarboxylic acid esters are useful, for example, as water-insoluble system surfactants, fiber softerners and emulsion stabilizers. However, it is quite unexpected that the above-mentioned PCA esters can promote percutaneous drug absorption.

Referring to general formula (I), the residue of aliphatic hydrocarbon represented by $R_2$ preferably contains 1 to about 24 carbon atoms. Said residue of aliphatic hydrocarbon is, for example, an alkyl group or an unsaturated hydrocarbyl group. Said alkyl group may be cyclic (i.e. cycloalkyl) or chain-like (either straight or branched). The unsaturated hydrocarbyl group also may be straight, branched or cyclic. The chain-like or acyclic alkyl group preferably contains 1 to 20 carbon atoms, the cyclic alkyl group preferably contains 6 to 12 carbon atoms, and the unsaturated hydrocarbyl group preferably contains 6 to 24 carbon atoms, in particular with 1 to 3 double bonds. The unsaturated hydrocarbyl group is more preferably acyclic. The chain-like alkyl group includes, among others, methyl, ethyl, n-propyl, n-butyl, n-heptyl, n-octyl, n-nonyl, n-decyl, n-undecyl, n-dodecyl, n-tridecyl, n-tetreadecyl, n-hexadecyl, n-octadecyl, n-eicosyl, iso-propyl, 2-methylhexyl, 2-ethylhexyl, 3,7-dimethyloctyl, 2-hexyldecyl, 2-octyldodecyl, 2,4,4-trimethyl-1-pentyl and methyloctyl. The cyclic alkyl group includes 2-cyclohexylethyl, cycloheptyl, cyclohexylmethyl, cyclooctyl, 4-cyclohexylbutyl, 3-cyclopentylpropyl and 5-methyl-2-isopropylcyclohexyl, among others. The unsaturated residue of aliphatic hydrocarbon is, for example, cis-3-hexenyl, oleyl, linoleyl or geranyl.

Referring to general formula (I), the alkyl group represented by $R_1$ preferably contains 1 to 5 carbon atoms and is, for example, methyl, ethyl, n-propyl, iso-propyl, n-butyl, t-butyl, iso-amyl or n-amyl.

More specifically, the PCA esters, when $R_2$ is an acylic alkyl group, include, but are not limited to 1-alkylpyrrolidonecarboxylic acid methyl esters, 1-alkylpyrrolidonecarboxylic acid ethyl esters, 1-alkylpyrrolidonecarboxylic acid n-propyl esters, 1-alkylpyrrolidonecarboxylic acid n-butyl esters, 1-alkylpyrrolidonecarboxylic acid n-heptyl esters, 1-alkylpyrrolidonecarboxylic acid n-octyl esters, 1-alkyl-pyrrolidonecarboxylic acid n-nonyl esters, 1-alkylpyrrolidonecarboxylic acid n-decyl esters, 1-alkylpyrrolidonecarboxylic acid n-undecyl esters, 1-alkylpyrrolidonecarboxylic acid n-dodecyl esters, 1-alkylpyrrolidonecarboxylic acid n-tridecyl esters, 1-alkylpyrrolidonecarboxylic acid n-tetradecyl esters, 1-alkylpyrrolidonecarboxylic acid n-hexadecyl esters, 1-alkylpyrrolidonecarboxylic acid n-octadecyl esters, 1-alkylpyrrolidonecarboxylic acid n-eicosyl esters, 1-alkylpyrrolidonecarboxylic acid iso-propyl esters, 1-alkylpyrrolidonecarboxylic acid 2-methylhexyl esters, 1-alkyl-pyrrolidonecarboxylic acid 2-ethylhexyl esters, 1-alkylpyrrolidonecarboxylic acid 3,7-dimethyloctyl esters, 1-alkylpyrrolidonecarboxylic acid 2-hexadecyl esters, 1-alkylpyrrolidonecarboxylic acid 2-octyldodecyl esters, 1-alkylpyrrolidonecarboxylic acid 2,4,4-trimethyl-1-pentyl esters, 1-alkylpyrrolidonecarboxylic acid methyloctyl esters, pyrrolidonecarboxylic acid methyl ester, pyrrolidonecarboxylic acid etheyl ester, pyrrolidonecarboxylic acid n-propyl ester, pyrrolidonecarboxylic acid n-butyl ester, pyrrolidonecarboxylic acid n-heptyl ester, pyrrolidonecarboxylic acid n-octyl ester, pyrrolidonecarboxylic acid n-nonyl ester, pyrrolidonecarboxylic acid n-decyl ester, pyrrolidonecarboxylic acid n-undecyl ester, pyrrolidonecarboxylic acid n-dodecyl ester, pyrrolidonecarboxylic acid n-tridecyl ester, pyrrolidonecarboxylic acid n-tetradecyl ester, pyrrolidonecarboxylic acid n-hexadecyl ester, pyrrolidonecarboxylic acid n-octadecyl ester, pyrrolidonecarboxylic acid n-eicosyl ester, pyrrolidonecarboxylic acid iso-propyl ester, pyrrolidonecarboxylic acid 2-methylhexyl ester, pyrrolidonecarboxylic acid 2-ethylhexyl ester, pyrrolidonecarboxylic acid 3,7-dimethyloctyl ester, pyrrolidonecarboxylic acid 2-hexadecyl ester, pyrrolidonecarboxylic acid 2-octyldodecyl ester, pyrrolidonecarboxylic acid 2,4,4-trimethyl-1-pentyl ester, and pyrrolidonecarboxylic acid methyloctyl ester. The alkyl group (1-alkyl) in the above compounds is, for example, methyl, ethyl, n-propyl, isopropyl, n-butyl, n-amyl or iso-amyl.

The PCA esters, when $R_2$ is a cyclic alkyl, include pyrrolidonecarboxylic acid 2-cyclohexylethyl ester, pyrrolidonecarboxylic acid cycloheptyl ester, pyrrolidonecarboxylic acid cyclohexylmethyl ester, pyrrolidonecarboxylic acid cyclooctyl ester, pyrrolidonecarboxylic acid cyclohexylbutyl ester, pyrrolidonecarboxylic acid 3-cyclopentylpropyl ester, pyrrolidonecarboxylic acid 5-methyl-2-isopropylcyclohexyl ester, 1-alkylpyrrolidonecarboxylic acid 2-cyclohexylethyl esters, 1-alkylpyrrolidonecarboxylic acid cycloheptyl esters, 1-alkylpyrrolidonecarboxylic acid 2-cyclohexylmethyl esters, 1-alkylpyrrolidonecarboxylic acid cyclooctyl esters, 1-alkylpyrrolidonecarboxylic acid 4-cyclohexylbutyl esters, 1-alkylpyrrolidonecarboxylic acid 3-cyclopentylpropyl esters, 1-alkylpyrrolidonecarboxylic acid 5-methyl-2-isopropylcyclohexyl esters, among others. The alkyl group (1-alkyl) in the above compounds is, for example, methyl, ethyl, n-propyl, iso-propyl, n-butyl, n-amyl or iso-amyl.

When $R_2$ is an unsaturated hydrocarbyl group, the PCA esters include, among others, pyrrolidonecarboxylic acid cis-3-hexenyl ester, pyrrolidonecarboxylic acid oleyl ester, pyrrolidonecarboxylic acid linoleyl ester, 1alkylpyrrolidonecarboxylic acid cis-3-hexenyl esters, 1-alkylpyrrolidonecarboxylic acid oleyl ester, and 1-alkylpyrrolidonecarboxylic acid linoleyl esters. The alkyl group (1-alkyl) in the above compounds is, for example, methyl, ethyl, n-propyl, iso-propyl, n-butyl, n-amyl or iso-amyl.

When $R_2$ is an unsaturated hydrocarbyl group, the PCA esters further include terpene alcohol-derived esters. Examples are pyrrolidonecarboxylic acid geranyl ester and 1-alkylpyrrolidonecarboxylic acid geranyl esters. The terpene alcohol moiety preferably contains 10 to 20 carbon atoms. The alkyl group (1-alkyl) in the above-mentioned compounds is, for example, methyl, ethyl, n-propyl, isopropyl, n-butyl, n-amyl, or iso-amyl.

The PCA esters to be used in accordance with the invention are substantially known compounds and can be produced by the known methods or modifications thereof. Among the PCA esters, the 1-alkyl substituted ones are producible by reacting the corresponding 2-pyrrolidone-carboxylic acid esters with an alkyl halide (the halide being e.g. chloride, bromide or iodide).

Among the PCA esters to be used in accordance with the invention, those containing a total of not less than 13 carbon atoms with an $R_1$ group of 1 to 5 carbon atoms and those containing a total of not less than 11 carbon atoms with a hydrogen atom as $R_1$, when used in combination with a highly polar hydrophilic compound, and those containing a total of 6 to 12 carbon atoms with a residue of aliphatic $C_{1-5}$ hydrocarbon as $R_2$, when used in combination with a nonpolar hydrophobic compound, can generally produce much increased absorption-promoting effect.

Examples of said hydrophilic compound are:

(1) Lower alcohols:

Preferred examples are monohydric alcohols containing 1 to 5 carbon atoms, such as methyl alcohol, ethyl alcohol, n-propyl alcohol, iso-propyl alcohol, n-butyl alcohol, isobutyl alcohol, sec-butyl alcohol, t-butyl alcohol, n-amyl alcohol, and iso-amyl alcohol.

(2) Glycerol and esters thereof:

The esters may be mono-, di- or triesters. The ester-forming acid is preferably a fatty acid containing 2 to 6 carbon atoms, more preferably acetic acid. Examples are glycerol monoacetate, glycerol diacetate and glycerol triacetate.

(3) Thioglycerols:

Any of mono-, di- and trithioglycerol may be used. An example is α-monothioglycerol.

(4) Lactic acid and esters thereof:

The ester-forming alcohol is preferably an aliphatic monohydric alcohol containing 1 to 4 carbon atoms. Examples are lactic acid, methyl lactate, ethyl lactate and butyl lactate.

(5) Cyclic ureas:

Five-membered and six-membered cyclic ureas are preferred. Examples are N,N'-dimethylethyleneurea, ethyleneurea and propyleneurea.

(6) Compounds of the general formula wherein $R_1$, $R_2$, $R_3$ and $R_4$ are each independently a hydrogen atom, a lower alkyl group containing 1 to 4 carbon atoms (e.g. methyl, ethyl, n-propyl, iso-propyl, n-butyl), a nitro group or an acyl group containing 1 or 2 carbon atoms:

Examples are urea, N-methylurea, N-ethylurea, N-butylurea, 1,1-dimethylurea, 1,3-dimethylurea, 1,1-diethylurea, 1,3-diethylurea, 1,1,3,3-tetramethylurea, N-actyl-N'-methylurea and nitrourea.

(7) Compounds of the general formula wherein $R_5$ is a hydrogen atom or a lower alkyl group containing 1 to 3 carbon atoms (e.g. methyl, ethyl, n-propyl, iso-propyl) and n is an integer of 3 to 5:

Examples are 2-pyrrolidone, N-methylpyrrolidone, N-methylpiperidone, caprolactam and N-methylcaprolactam.

(8) Compounds of the general formula wherein $R_6$, $R_7$ and $R_8$ are each independently a hydrogen atom or a lower alkyl group containing 1 to 3 carbon atoms (e.g. methyl, ethyl, n-propyl, iso-propyl):

Examples are formamide, N-methylformamide, N,N-dimethylformamide, N,N-diethylformamide, acetamide, N-methylacetamide, N,N-dimethylacetamide, N,N-diethylacetamide, propionamide, N-methylpropionamide, N,N-dimethylpropionamide and N,N-diethylpropionamide.

(9) Alkylene glycols:

The alkylene preferably contains 2 to 8 carbon atoms. Examples are ethylene glycol, 1,3-propanediol, 1,2-propanediol, butanediol, pentanediol, 2-methyl-2,4-pentanediol and 2-ethyl-1,3-hexanediol.

(10) Monoalkyl ethers of mono- or diethylene glycol:

The alkyl group in the monoalkyl ether preferably contains 1 to 2 carbon atoms. Examples are ethylene glycol monomethyl ether and ethylene glycol monoethyl ether.

(11) Lactones:

Four-membered and five-membered ring lactones are preferred. Examples are β-propiolactone and γ-butyrolactone.

Said hydrophobic compound includes, among others:

(1) Alcohols containing 7 to 20 carbon atoms:

Said alcohols may be straight or branched, or unsaturated. Examples are straight-chain alcohols, such as lauryl alcohol, branched alcohols, such as iso-stearyl alcohol, and unsaturated alcohols, such as oleyl alcohol.

(2) Aliphatic hydrocarbons containing 5 to 30 carbon atoms, which may optionally be halo-substituted:

Said aliphatic hydrocarbons may be straight, branched or cyclic. Preferred as the substituent halogen atoms are bromine and chlorine.

When acyclic, the aliphatic hydrocarbon moiety is preferably an alkyl, alkenyl or alkadienyl (containing two unsaturated bonds) group containing 5 to 30 (more preferably 6 to 24) carbon atoms and, when cyclic, it is preferablly a monocyclic or dicyclic or bicyclic one. When monocyclic, it preferably contains 6 to 10 carbon atoms and may be substituted by at least one saturated or unsaturated hydrocarbyl group containing 1 to 3 carbon atoms, such as alkyl (e.g. methyl) or —C(C$_3$)=CH$_2$. Furthermore, it may consist of an alkylene group and two monocycles connected with each other via said alkylene gruop. When bicyclic, it may be substituted by at least one lower alkyl group such as methyl. Examples are n-pentane, n-hexane, n-heptane, n-octane, n-nonane, n-decane, n-undecane, n-dodecane, n-tetradecane, n-hexadecane, n-octadecane, 2-methylpentane, 2-methylhexane, 2,3-dimethylhexane, 2-methylnonane, 2,6-dimethyloctane, 2,2,4,4,6,8,8-heptamethylnonane, pristane, squalane, light liquid paraffin, paramenthane, limonene, hydrogenated limonene dimer, cyclohexane, 1,3-dimethylcyclohexane, cyclooctane, isobutylcyclohexane, cyclododecane, methyldecalin, decalin, octyl bromide, decyl bromide, dodecyl bromide, hexadecyl bromide, dodecyl chloride and dibromododecane.

(3) Aliphatic carboxylic acid alcohol esters containing a total of 11 to 26, preferably 12 to 20, carbon atoms:

Preferred alcohol moieties are derived from monohydric alcohols containing 1 to 6 carbon atoms, such as methyl alcohol, ethyl alcohol, n-propyl alcohol, iso-propyl alcohol, n-butyl alcohol, iso-butyl alcohol, sec-butyl alcohol, t-butyl alcohol, n-amyl alcohol, iso-amyl alcohol and n-hexyl alcohol. Preferred carboxylic acid moieties are derived from fatty acids containing 10 to 20 carbon atoms, more preferably 12 to 18 carbon atoms. Examples of said esters are methyl laurate, ethyl laurate, hexyl laurate, isopropyl myristate, isopropyl palmitate, methyl stearate, butyl stearate and methyl oleate.

(4) Mono- or diethers containing 10 to 24 carbon atoms:

Examples are alkyl monoethers, such as dipentyl ether, dihexyl ether, dioctyl ether, didodecyl ether, methoxydecane and ethoxydecane; alicycle-containig ethers, such as 1,8-cineole; and alkyl diethers, such as ethylene glycol dibutyl ether, ethylene glycol dipropyl ether and ethylene glycol dioctyl ether. Preferably, they contain 10 to 18 carbon atoms, more preferably 12 to 18 carbon atoms.

(5) Ketones containing 11 to 15, preferably 12 to 14 carbon atoms:

Preferred are aliphatic ketones, such as 2-undecanone, 3-undecanone, 4-undecanone, 5-undecanone, 6-undecanone, 3-dodecanone, 4-dodecanone, 5-dodecanone, 2-tridecanone, 3-tridecanone, 7-tridecanone, 8-pentadecanone and 3-hexadecanone.

Generally, the PCA ester and the above-mentioned hydrophilic or hydrophobic compound are used in a proportion of 99:1 to 1:99 by weight. For the combination of PCA ester and hydrophilic compound, preferred proportions are within the range of 25:75 to 1:99 by weight and, for the combination of PCA ester and hydrophobic compound, 75:25 to 99:1 by weight.

The composition for external drug application increases the percutaneous absorbability of drugs, so that drugs may be administered in the presence of said composition. Preferably, however, drugs are incorporated into the composition according to the invention in advance.

As far as administrable percutaneously, any drug may be incorporated into the composition for external drug application according to the invention. Drugs intended to produce local effects can penetrate into the depth, and drugs intended to produce systemic effects can be transferred to the blood circulation rapidly. The drugs preferably have a molecular weight of not more than 1,000, more preferably not more than 500.

As locally acting drugs, there may be mentioned local anesthetics (e.g. procaine hydrochloride, tetracaine hydrochloride, dibucaine hydrochloride, lidocaine, lidocaine hydrochloride, piperocaine acetate), antihistaminics (e.g. diphenhydramine hydrochloride, chlorpheniramine maleate, brompheniramine maleate, diphenylimidazole, cremizole hydrochloride), antibiotics (e.g. lincomycin, penicillin G, erythromycin, tetracycline hydrochloride, clindamycin, kanamicin, oxytetracycline, chloramphenicol, fradiomycin, nystatin, gramicidin hydrochloride, bacitracin), and antimycotics (e.g. griseofulvan, N-methyl-N-(3-tolyl)-thiosemicarbamic acid 2-naphthyl ester, diamthazole hydrochloride, aureothricin, trichomycin, pyrrolnitrin, 5-fluorocytosine).

As systemic drugs, there may be mentioned benzodiazepines (e.g. diazepam, nitrazepam, flunitrazepam, lorazepam, prazepam, fludiazepam, clonazepam), diuretics (e.g. bendroflumethiazide, polythiazide, methyclothiazide, trichlormethiazide, cyclopenthiazide, benzylhydrochlorothiazide, hydrochlorothiazide, bumetanide), antihypertensive agents (e.g. clonidine), antihistaminics [e.g. aminoethers (e.g. diphenhydramine, carbinoxamine, diphenylpyraline), ethylenediamines (e.g. phenbenzamine), monoamines (e.g. chlorpheniramine)], nonsteroid antiinflammatories (e.g. indomethacin, ibuprofen, ibufenac, alclofenac, diclofenac, mefenamic acid, flurubiprofen, flufenamic acid, ketoprofen), antimalignant-tumor agents [e.g. 5-fluorouracil, 1-(2-tetrahydrofuryl)-5-fluorouracil, cytarabine, broxuridine], steroidal antiinflammatories (e.g. cortisone, hydrocortisone, prednisolone, triamcinolone, dexamethasone, betamethasone), antiepileptics (e.g. ethosuximide), antiarrythmic agents (e.g. ajmaline, prajmalin, pindolol, propranolol, quinidine), pyschotropic agents (e.g. chlofluperidol, trifluperidol, haloperidol, moperone), scopolamines (e.g. methylscopolamine, butylscopolamine), chlorpromazine, atropines (e.g. methylatropine bromide, methylanisotropine bromide), vasodilators (e.g. isosorbide dinitrate, nitroglycerin, pentaerythritol tetranitrate, propatyl nitrate, dipyridamole) and antibiotics [e.g. tetracyclines (e.g. tetracycline, oxytetracycline, metacycline, doxycycline, minocycline), chloramphenicols, erythromycins].

The drugs are incorporated into the composition in amounts sufficient to produce desired therapeutic or pharmacologic effects, which amounts may vary depending on the drug species, patient's body weight and symptoms, and other factors and may appropriately be selected according to these factors. The drugs are used generally in amount of 0.01 to 20% by weight, preferably 0.2 to 10% by weight, based on the whole base composition comprising the PCA ester and others.

The drug amount for incorporation is not limited to the above since the dose of drugs can be adjusted by increasing or decreasing the area of the application site on the skin where the drug composition in question is applied.

The composition for external drug application in accordance with the invention is administered to the skin either as it is or in the form of an unemulsifiable preparation for external use, such as ointment, plaster, lotion, adhesive tape, impregnant or gel, as made by addition of a pharmaceutically acceptable known carrier. The impregnant is prepared, for example, by allowing said composition for external drug application or a composition made by adding a third known component to said composition to be absorbed on an appropriate adsorbent (e.g. gauze, filter paper, porous membrane) and is applied to the skin generally under fixation by means of an adhesive tape for surgery. The gel is prepared, for example, producing a gel using, for instance, dibenzylidenesorbitol [e.g. GELOL D ® (Shin Nippon Rika Kogyo)] and spreading the gel onto a support member. The adhesive base for the adhesive tape may be a per se known one, such as an acrylic copolymer, a polyvinyl ether compound or an adhesive rubber mixture. Other external preparations also can be prepared easily by the per se known means.

The following examples and test examples illustrate the invention is further detail. It is to be noted, however, that they are by no means limitative of the scope of the present invention.

PRODUCTION EXAMPLE 1

Producton of 2-pyrrolidone-5-carboxylic acid n-heptyl ester

A 200-ml eggplant-shaped flask equipped with a condenser and a mechanical stirrer was charged with 6.5 g (0.05 mole) of 2-pyrrolidone-5-carboxylic acid, 23.2 g (0.20 mole) of n-heptyl alcohol, a catalytic amount of concentrated sulfuric acid and 40 ml of benzene and the mixture was refluxed for 3.5 hours. The reaction mixture was cooled to room temperature and poured into saturated aqueous $NaHCO_3$, followed by extraction with benzene. Washing, drying, solvent removal and distillation under reduced pressure as performed in the conventional manner gave 7.4 g of yellow 2-pyrrolidone-5-carboxylic acid n-heptyl ester. Boiling point: 186°–188° C./3 mm Hg.

Other PCA esters in which $R_1$ is hydrogen can be produced essentially by the procedure of the above Production Example 1.

Production Example 2

Production of 1-methyl-2-pyrrolidone-5-carboxylic acid n-dodecyl ester:

A three-necked flask equipped with a Dimroth condenser, a stirrer and a dropping funnel was charged with 3.0 g (0.075 mol) of a 60% NaH-in-mineral oil dispersion and 50 ml of petroleum ether. The contents were stirred, then stirring was discontinued and the NaH was allowed to precipitate. Thereafter, most of the petroleum ether was removed, 200 ml of toluene was added, and the mixture was stirred. Thereto was added dropwise a toluene solution of 17.4 g (0.059 mole) of 2-pyrrolidone-5-carboxylic acid n-dodecyl ester. After 2 hours of refluxing, the mixture was cooled to room temperature, then a toluene solution of 25 g (0.176 mol)

of methyl iodide was added dropwise and the resulting mixture was refluxed for 5 hours.

The reaction mixture was filtered, the solvent was distilled off, and the residue was purified to give 11.9 g of 1-methyl-2-pyrrolidone-5-carboxylic acid n-dodecyl ester as a light-yellow liquid. The yield was 64.9% (from 2-pyrrolidone-5-carboxylic acid n-dodecyl ester).

Other 1-alkyl substituted PCA esters also can be produced essentially by the procedure of the above Production Examples.

Examples 1 to 52

| Basic formulation | weight % |
|---|---|
| (1) Drug substance | 1 |
| (2) Hydrophilic or hydrophobic compound | 74 |
| (3) PCA ester | 25 |

Using the respective materials given in Table 1 as the materials (1), (2) and (3), liquid compositions according to the above formulation were prepared by first mixing (2) with (3) and then dissolving (1) in the resultant mixture of (2) and (3). In the table, PAC means pyrrolidonecarboxylic acid (also in Tabel 2, the same shall apply).

Examples 53 to 73

| Basic formulation | weight % |
|---|---|
| (1) Drug substance | 1 |
| (2) Hydrophilic or hydrophobic compound | 24 |
| (3) PCA ester | 75 |

Using the respective materials given in Table 1 as the materials (1), (2) and (3), liquid compositions according to the above formulation were prepared by first mixing (2) with (3) and then dissolving (1) in the resultant mixture of (2) and (3).

Control Formulation 1

| | Weight % |
|---|---|
| (1) Drug substance | 1 |
| (2) Hydrophilic or hydrophobic compound | 99 |

Compositions corresponding to the compositions of the above examples but lacking in component (3) were prepared by using each material given in Table 1 as (2) and dissolving (1) in (2).

Comparative Examples 1 to 5

| | | Weight % |
|---|---|---|
| (1) | Drug substance | 1 |
| (2) | Hydrophilic or hydrophobic compound | 74 |
| (3) | Pyrrolidonecarboxylic acid monoglyceride ester | 25 |

(R being the oleic or stearic acid residue)

Comparative Example 6 to 15

| | Weight % |
|---|---|
| (1) Drug substance | 1 |
| (2) Hydrophilic or hydrophobic compound | 24 |
| (3) Pyrrolidonecarboxylic acid or sodium salt thereof | 75 |

Test Example 1

The compositions of Examples 1 to 73, Control Formulation 1 and Comparative Examples 1 to 15 were tested for percutaneous drug permeations using the excised rat abdominal skin. The results are shown in Table 1 and Table 2.

In Table 1 and Table 2, the Q value means the following:

$$Q = C/D$$

where C = the amount of drug which had permeated the skin in each example or comparative example; D = the amount of drug which had permeated the skin in Control Formulation 1.

[Method of measurement]

The rat skin was fixed on a glass permeation cell such that the exterior surface of the skin was in contact with one of the above compositions and the reverse side in contact with physiological saline. That portion of drug which had permeated the skin into physiological saline was assayed by high-performance liquid chromatography. This test was conducted in a hermetically closed container.

Example 74 and Test Example 2

| (1) Propranolol hydrochloride | 1 g |
|---|---|
| (2) 1,2-Propanediol | 0–100 g |
| (3) Pyrrolidonecarboxylic acid n-dodecyl ester | 100–0 g |

Figure 1:
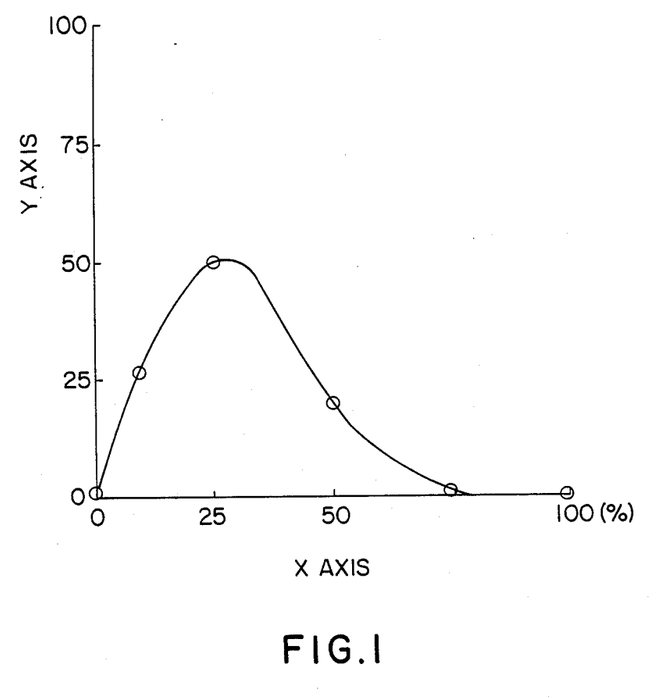

Various liquid mixtures were prepared from component (2) and component (3) varying the proportion (by weight) therebetween from 100:0 to 0:100 and propranolol hydrochloride was dissolved in the mixtures to the concentration of 1%. Each composition thus obtained was tested for skin permeating ability in the same manner as in Table Example 1. The results obtained are shown in FIG. 1, wherein the Y axis stands for the ratio in drug permeation quantity between each of the above compositions and the base wholly consisting of 100 g of component (2) alone and the X axis for the content, in weight percent, of component (3) in the total of component (2) and component (3).

Example 75 and Test Example 3

| (1) Propanolol hydrochloride | 1 g |
|---|---|
| (2) DRAGOSANTOL | 0–100 g |
| (3) Pyrrolidonecarboxylic acid methyl ester | 100–0 g |

Figure 2:
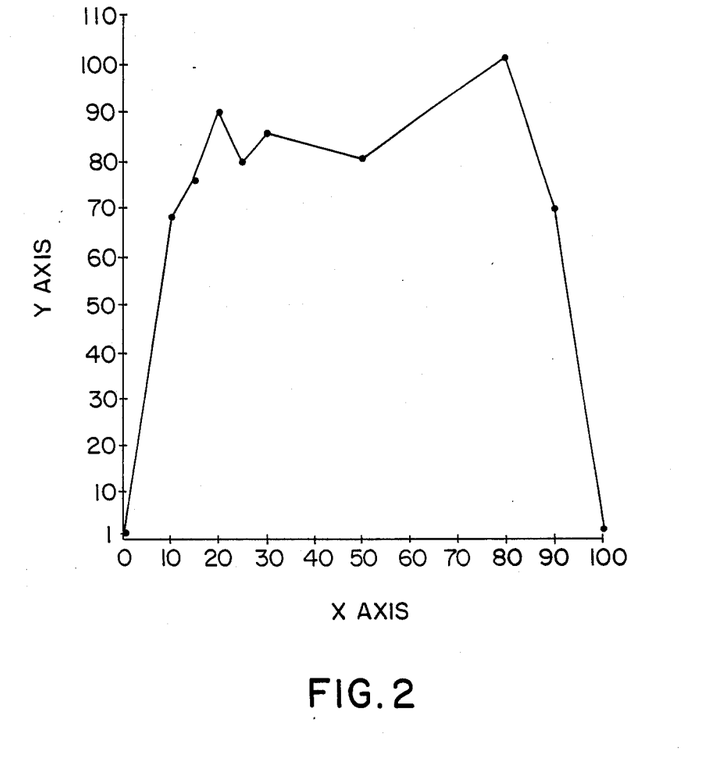

Various liquid mixtures were prepared from component (2) and component (3) varying the proportion (by weight) therebetween from 100:0 to 0:100 and propranolol hydrochloride was dissolved in the mixtures to the concentration of 1%. Each composition thus obtained was tested for skin permeating ability in the same manner as in Test Example 1. The results obtained are shown in FIG. 2, wherein the Y axis stands for the ratio in drug permeation quantity between each of the above compositions and the base wholly consisting of 100 g of component (2) alone and the X axis for the content, in weight percent, of component (3) in the total of component (2) and component (3). DRAGOSANTOL is a product of Dragoco, Japan and is composed of 85% of α-bisabolol and 15% of farnesol.

TABLE 1

| Example | Drug | Hydrophilic or hydrophobic compound | PCA ester | Q value |
|---|---|---|---|---|
| 1 | Propranolol hydrochloride | Dimethylacetamide | 1-Methyl-PCA n-heptyl ester | 19.1 |
| 2 | Diazepam | N—Methylpyrrolidone | 1-Methyl-PCA n-dodecyl ester | 5.3 |
| 3 | Indomethacin | 1,2-Propanediol | 1-Methyl-PCA n-octadecyl ester | 3.8 |
| 4 | Sodium salicylate | Ethanol | 1-Ethyl-PCA n-hexyl ester | 32.5 |
| 5 | Propanolol hydrochloride | N—Methylpyrrolidone | 1-Ethyl-PCA n-decyl ester | 27.2 |
| 6 | Indomethacin | N—Methylpyrrolidone | 1-n-Propyl-PCA n-amyl ester | 4.2 |
| 7 | Diazepam | N,N'—Dimethylethyleneurea | 1-n-Propyl-PCA n-tetradecyl ester | 7.3 |
| 8 | Metoclopramide hydrochloride | Methyl lactate | 1-n-Butyl-PCA n-butyl ester | 2.6 |
| 9 | Metoclopramide hydrochloride | Methyl cellosolve | 1-n-Butyl-PCA n-octyl ester | 16.5 |
| 10 | Indomethacin | Ethanol | 1-n-Butyl-PCA n-eicosyl ester | 5.7 |
| 11 | Theophylline | 1,2-Propanediol | 1-n-Amyl-PCA n-propyl ester | 8.3 |
| 12 | Metoclopramide hydrochloride | Methyl cellosolve | 1-n-Amyl-PCA n-dodecyl ester | 26.3 |
| 13 | Diazepam | 2,3-Butanediol | 1-n-Amyl-PCA n-eicosyl ester | 3.1 |
| 14 | Indomethacin | 2,3-Butanediol | 1-Methyl-PCA 2-methylhexyl ester | 5.1 |
| 15 | Theophylline | Ethanol | 1-Ethyl-PCA 3,7-dimethyloctyl ester | 44.3 |
| 16 | Propranolol hydrochloride | Methyl lactate | 1-n-Propyl-PCA 2-ethylhexyl ester | 10.7 |
| 17 | Sodium salicylate | Dimethylacetamide | 1-n-Butyl-PCA n-hexyldecyl ester | 27.5 |
| 18 | Sodium salicylate | N—Methylpyrrolidone | 1-n-Amyl-PCA isopropyl ester | 8.9 |
| 19 | Indomethacin | Methyl lactate | 1-n-Amyl-PCA 2-octyldodecyl ester | 7.4 |
| 20 | Metoclopramide hydrochloride | 1,2-Propanediol | 1-Isopropyl-PCA n-amyl ester | 17.2 |
| 21 | Propranolol hydrochloride | Methyl cellosolve | 1-Isopropyl-PCA n-dodecyl ester | 11.8 |
| 22 | Propranolol hydrochloride | N,N'—Dimethylethyleneurea | 1-Isoamyl-PCA n-propyl ester | 6.6 |
| 23 | Indomethacin | Dimethylacetamide | 1-Isoamyl PCA n-eicosyl ester | 4.5 |
| 24 | Theophylline | Dimethylacetamide | 1-Isopropyl-PCA isoamyl ester | 16.1 |
| 25 | Propranolol hydrochloride | Ethanol | 1-Isopropyl-PCA 2-octyldecyl ester | 13.8 |
| 26 | Sodium salicylate | 1,2-Propanediol | 1-Isoamyl-PCA isopropyl ester | 7.5 |
| 27 | Theophylline | N—Methylpyrrolidone | 1-Isoamyl-PCA 3,7-dimethyloctyl ester | 36.2 |
| 28 | Metoclopramide hydrochloride | N—Methylpyrrolidone | 1-Isoamyl-PCA 2-octyldodecyl ester | 29.7 |
| 29 | Lidocaine | N,N'—Dimethylethyleneurea | 1-Methyl-PCA cyclohexylmethyl ester | 3.6 |
| 30 | Diazepam | Methyl lactate | 1-Methyl-PCA 4-cyclohexylbutyl ester | 9.1 |
| 31 | Sodium salicylate | N,N'—Dimethylethyleneurea | 1-n-Propyl-PCA 2-cyclohexylethyl ester | 33.7 |
| 32 | Theophylline | 2,3-Butanediol | 1-n-Amyl-PCA 4-cyclohexylbutyl ester | 13.5 |
| 33 | Sodium salicylate | Methyl cellosolve | 1-Methyl-PCA oleyl ester | 45.5 |
| 34 | Metoclopramide hydrochloride | N—Methylpyrrolidone | 1-Ethyl-PCA cis-3-hexenyl ester | 14.8 |
| 35 | Lidocaine | 1,2-Propanediol | 1-Isopropyl-PCA cis-3-hexenyl ester | 8.3 |
| 36 | Diazepam | Ethanol | 1-Isoamyl-PCA oleyl ester | 4.0 |
| 37 | Propranolol hydrochloride | Dimethylacetamide | PCA n-heptyl ester | 12.7 |
| 38 | Propranolol hydrochloride | N—Methylpyrrolidone | PCA n-octyl ester | 6.5 |
| 39 | Diazepam | N—Methylpyrrolidone | PCA n-decyl ester | 3.5 |
| 40 | Propranolol hydrochloride | 1,2-Propanediol | PCA n-dodecyl ester | 42.0 |
| 41 | Propranolol hydrochloride | Dimethylacetamide | PCA n-hexadecyl ester | 22.1 |
| 42 | Lidocaine | Ethanol | PCA n-eicosyl ester | 3.3 |
| 43 | Chlorpheniramine maleate | N,N'—Dimethylethyleneurea | PCA 2-methylhexyl ester | 6.2 |
| 44 | Erythromycin | Ethylene glycol monoethyl ether | PCA 2-ethylhexyl ester | 7.1 |
| 45 | Pindolol | 1,2-Propanediol | PCA 3,7-dimethyloctyl ester | 11.0 |
| 46 | 5-Fluorouracil | 1,2-Propanediol | PCA 2-hexyldecyl ester | 27.0 |
| 47 | N—Methyl-N—(3-tolyl)-thiocarbamic acid naphthyl ester | t-Butyl alcohol | PCA cis-3-hexenyl ester | 4.3 |
| 48 | Propranolol hydrochloride | 1,2-Propanediol | PCA oleyl ester | 40.0 |
| 49 | Clonidine hydrochloride | Ethanol | PCA geranyl ester | 7.4 |
| 50 | Prednisolone | 1,2-Propanediol | PCA 2-cyclohexylethyl ester | 2.5 |
| 51 | Diclofenac sodium | Ethyl lactate | PCA 4-cyclohexylbutyl ester | 6.4 |

TABLE 1-continued

| Example | Drug | Hydrophilic or hydrophobic compound | PCA ester | Q value |
|---|---|---|---|---|
| 52 | Indomethacin | Ethanol | PCA methyl ester | 3.2 |
| 53 | Propranolol hydrochloride | DRAGOSANTOL | 1-Methyl-PCA methyl ester | 7.7 |
| 54 | Theophylline | Oleyl alcohol | 1-n-Amyl-PCA methyl ester | 6.9 |
| 55 | Sodium salicylate | Lauryl alcohol | 1-n-Amyl-PCA ethyl ester | 11.3 |
| 56 | Diazepam | DRAGOSANTOL | 1-Methyl-PCA isopropyl ester | 4.6 |
| 57 | Propranolol hydrochloride | Methyl linoleate | 1-Ethyl-PCA isoamyl ester | 5.0 |
| 58 | Metoclopramide hydrochloride | Methyl linoleate | 1-n-Butyl-PCA isopropyl ester | 4.1 |
| 59 | Theophylline | Oleyl alcohol | 1-Isopropyl-PCA methyl ester | 13.7 |
| 60 | Sodium salicylate | DRAGOSANTOL | 1-Isoamyl-PCA ethyl ester | 9.4 |
| 61 | Metoclopramide hydrochloride | Methyl linoleate | 1-Isopropyl-PCA isopropyl ester | 6.2 |
| 62 | Propranolol hydrochloride | DRAGOSANTOL | PCA methyl ester | 7.4 |
| 63 | Sodium salicylate | Lauryl alcohol | PCA methyl ester | 7.0 |
| 64 | Theophylline | DRAGOSANTOL | PCA methyl ester | 28.0 |
| 65 | Metoclopramide hydrochloride | Lauryl alcohol | PCA methyl ester | 25.7 |
| 66 | Diazepam | DRAGOSANTOL | PCA ethyl ester | 2.2 |
| 67 | Theophylline | Isopropyl myristate | PCA ethyl ester | 8.6 |
| 68 | Sodium salicylate | Oleyl alcohol | PCA ethyl ester | 11.1 |
| 69 | Propranolol hydrochloride | DRAGOSANTOL | PCA ethyl ester | 5.1 |
| 70 | Indomethacin | DRAGOSANTOL | PCA isopropyl ester | 1.5 |
| 71 | Diclofenac sodium | Lauryl alcohol | PCA isopropyl ester | 5.6 |
| 72 | Theophylline | Methyl linoleate | PCA isopropyl ester | 13.7 |
| 73 | Theophylline | Lauryl alcohol | PCA isoamyl ester | 7.9 |

TABLE 2

| Comparative Example | Drug | Hydrophilic or hydrophobic compound | PCA compound | Q value |
|---|---|---|---|---|
| 1 | Propranolol hydrochloride | Dimethylacetamide | PCA monooleoylglycerol ester | 0.8 |
| 2 | Propranolol hydrochloride | N—Methylpyrrolidone | PCA monooleoylglycerol ester | 0.9 |
| 3 | Diazepam | N—Methylpyrrolidone | PCA monostearoylglycerol ester | 0.7 |
| 4 | Theophylline | 1,2-Propanediol | PCA monostearoylglycerol ester | 1.3 |
| 5 | Lidocaine | Ethanol | PCA monooleoylglycerol ester | 1.1 |
| 6 | Propranolol hydrochloride | Oleyl alcohol | PCA | 0.7 |
| 7 | Indomethacin | Oleyl alcohol | PCA sodium salt | 0.5 |
| 8 | Diazepam | DRAGOSANTOL | PCA | 1.2 |
| 9 | Theophylline | Methyl linoleate | PCA | 1.5 |
| 10 | Metoclopramide hydrochloride | Lauryl alcohol | PCA sodium salt | 0.8 |
| 11 | Propranolol hydrochloride | DRAGOSANTOL | PCA | 0.6 |
| 12 | Theophylline | Oleyl alcohol | PCA | 0.5 |
| 13 | Diazepam | Lauryl alcohol | PCA sodium salt | 1.0 |
| 14 | Metoclopramide hydrochloride | Methyl linoleate | PCA sodium salt | 0.9 |
| 15 | Propranolol hydrochloride | Oleyl alcohol | PCA sodium salt | 0.8 |

What is claimed is:

1. In a method of drug administration, wherein the improvement is the use of a percutaneous promoter compound of the formula (I)

wherein $R_1$ is a hydrogen atom or a $C_1$–$C_5$ alkyl group and $R_2$ is an alkyl group having 1–24 carbon atoms or an unsaturated hydrocarbonyl group having 1–24 carbon atoms.

2. The method according to claim 1, wherein $R_1$ in general formula (I) is a hydrogen atom.

3. The method according to claim 1, wherein $R_1$ in general formula (I) is an alkyl group.

4. The method according to claims 1, 2 or 3, wherein said compound contains a total of 6 to 12 carbon atoms and $R_2$ is a residue of an aliphatic hydrocarbon containing 1 to 5 carbon atoms.

5. The method according to claim 4, which further contains a hydrophobic compound to enhance the absorptive properties of the composition, said hydrophobic compound being selected from the group consisting essentially of alcohols containing 7 to 20 carbon atoms, aliphatic hydrocarbons containing 5 to 30 carbon atoms or such aliphatic hydrocarbons substituted with halogen, aliphatic carboxylic acid alcohol esters containing 11 to 26 carbons, aliphatic mono- or di-esters containing 10 to 24 carbon atoms and aliphatic ketones containing 11 to 15 carbon atoms.

6. The method according to claim 1, wherein said compound contains a total of not less than 13 carbon atoms and $R_1$ is an alkyl group containing 1 to 5 carbon atoms.

7. The method according to claim 2, wherein said compound contains a total of not less than 11 carbon atoms.

8. The method according to claim 6 or 7, which further contains a hydrophilic compound to enhance the absorptive properties of the compound, said hydrophilic compound being a monohydric alcohol having 1 to 5 carbon atoms, mono-, di and tri-esters of said monohydric alcohols with fatty acids containing 2 to 6 carbon atoms, thioglycerols, lactic acid and esters thereof, 5 and 6-membered cyclic ureas, compounds of the general formula $$\begin{matrix} R_1 & O & R_3 \\ \diagdown & \| & \diagup \\ & N-C-N & \\ \diagup & & \diagdown \\ R_2 & & R_4 \end{matrix} \quad (II)$$

wherein $R_1$, $R_2$ and $R_3$ and $R_4$ are each independently a hydrogen atom, a lower alkyl group containing 1 to 4 carbon atoms, a nitro group or an acyl group containing 1 to 4 carbon atoms, a nitro group or an acyl group containing 1 to 2 carbon atoms, compounds of the general formula $$\begin{matrix} & O & \\ & \| & \\ & C & \\ R_5-N & & \\ & \diagdown & \diagup \\ & (CH_2)_n & \end{matrix} \quad (III)$$

wherein $R_5$ is a hydrogen atom or a lower alkyl group containing 1 to 3 carbon atoms and n is an integer of 3 to 5, compounds of the general formula $$R_8CON\begin{matrix} R_6 \\ \diagup \\ \diagdown \\ R_7 \end{matrix} \quad (IV)$$

wherein $R_6$, $R_7$ and $R_8$ are each independently a hydrogen atom or a lower alkyl group containing 1 to 3 carbon atoms, alkylene glycols containing 2 to 8 carbon atoms, monoalkyl ethers of mono- or di-ethylene glycol in which the alkyl group contains 1 or 2 carbon atoms and 5 or 6-membered ring lactones.

9. A method according to claim 1, wherein the drug is an anesthetic.

10. A method according to claim 1, wherein the drug is an antihistamine.

11. A method according to claim 1, wherein the drug is an antibiotic.

12. A method according to claim 1, wherein the drug is an antimycotic.

13. A method according to claim 1, wherein the drug is a diuretic.

14. A method according to claim 1, wherein the drug is an antihypertensive agent.

15. A method according to claim 1, wherein the drug is an anti-inflammatory agent.

16. A method according to claim 1, wherein the drug is an antiepileptic agent.

17. A method according to claim 1, wherein the drug is a psychotropic agent.

18. A method according to claim 1 wherein the drug is an antiarrythmic agent.

19. A method according to claim 1 wherein the drug is a vasodilator.

* * * * *